United States Patent
Cohen et al.

(10) Patent No.: US 8,642,566 B2
(45) Date of Patent: Feb. 4, 2014

(54) THERAPEUTIC APPROACHES FOR TREATING NEUROINFLAMMATORY CONDITIONS

(75) Inventors: Daniel Cohen, Le Vesinet (FR); Serguei Nabirochkin, Chatenay Malabry (FR); Ilya Chumakov, Vaux le Penil (FR)

(73) Assignee: Pharnext, Issy les Moulineaux (FR)

( * ) Notice: Subject to any disclaimer, the term of this patent is extended or adjusted under 35 U.S.C. 154(b) by 0 days.

(21) Appl. No.: 13/260,773

(22) PCT Filed: Mar. 29, 2010

(86) PCT No.: PCT/EP2010/054068
§ 371 (c)(1),
(2), (4) Date: Jan. 12, 2012

(87) PCT Pub. No.: WO2010/115741
PCT Pub. Date: Oct. 14, 2010

(65) Prior Publication Data
US 2012/0108528 A1    May 3, 2012

(30) Foreign Application Priority Data
Mar. 30, 2009    (EP) .................................... 09305265

(51) Int. Cl.
*A61K 31/7028* (2006.01)

(52) U.S. Cl.
USPC .......................................................... 514/25

(58) Field of Classification Search
USPC .......................................................... 514/25
See application file for complete search history.

(56) References Cited

U.S. PATENT DOCUMENTS

2006/0034847 A1 *  2/2006  Yun et al. ................... 424/146.1

OTHER PUBLICATIONS

Ubogu, E. et al. "Determinants of CCL5-driven mononuclear cell migration across the blood brain barrier. Implications for therapeutically modulating neuroinflammation" *Journal of Neuroimmunology*, 2006, pp. 132-144, vol. 179, Nos. 1-2.
Man, S. et al. "Inflammatory Cell Migration into the Central Nervous System: A Few New Twists on an Old Tale" *Brain Pathology*, 2007, pp. 243-250, vol. 17, No. 2.
Bonneh-Barkay, D. et al. "Brain Extracellular Matrix in Neurodegeneration" *Brain Pathology*, 2009, pp. 573-585, vol. 19, No. 4.
Paintlia, A. S. et al. "Combined medication of lovastatin with rolipram suppresses severity of experimental autoimmune encephalomyelitis" *Experimental Neurology*, 2008, pp. 168-180, vol. 214, No. 2.
Ifergan, I. I. et al. "Statins Reduce Human Blood-Brain Barrier Permeability and Restrict Leukocyte Migration: Relevance to Multiple Sclerosis" *Annals of Neurology*, 2006, pp. 45-55, vol. 60, No. 1.
Tan, A. et al. "Lovastatin Induces Fibroblast Apoptosis In Vitro and In Vivo: A Possible Therapy for Fibroproliferative Disorders" *American Journal of Respiratory and Critical Care Medicine*, 1999, pp. 220-227, vol. 159, No. 1.
Sanchez, A. J. et al. "Rolipram impairs NF-κB activity and MMP-9 expression in experimental autoimmune encephalomyelitis" *Journal of Neuroimmunology*, 2005, pp. 13-20, vol. 168.
Written Opinion in International Application No. PCT/EP2010/054068, Oct. 7, 2010, pp. 1-13.

* cited by examiner

*Primary Examiner* — Wu-Cheng Winston Shen
*Assistant Examiner* — Yih-Horng Shiao
(74) *Attorney, Agent, or Firm* — Saliwanchik, Lloyd & Eisenschenk

(57) ABSTRACT

The present invention relates to novel compositions which can be used for the treatment of neuroinflammation, in particular in subjects having a neurodegenerative, autoimmune, infectious, toxic or traumatic disorder. More particularly, the invention relates to combined therapies for treating neuroinflammation. The invention also discloses new methods for treating neuroinflammation pathological conditions in a subject.

9 Claims, 1 Drawing Sheet

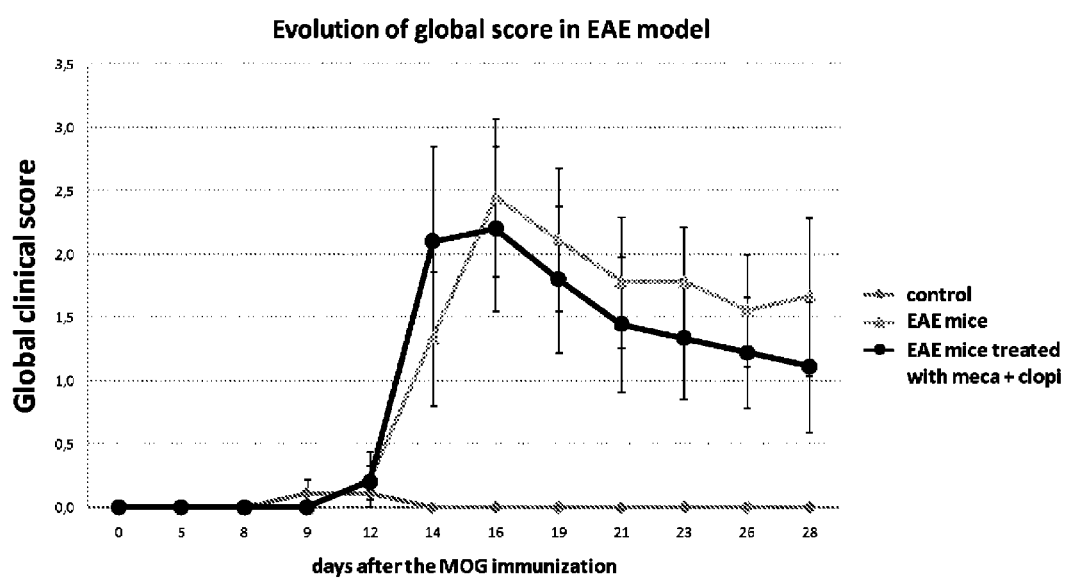

THERAPEUTIC APPROACHES FOR TREATING NEUROINFLAMMATORY CONDITIONS

CROSS-REFERENCE TO RELATED APPLICATION

This application is the U.S. national stage application of International Patent Application No. PCT/EP2010/054068, filed Mar. 29, 2010.

FIELD OF THE INVENTION

The present invention relates generally to the fields of pharmacology and medicine. More specifically, the present invention relates to novel combinatorial therapies for the treatment of neuroinflammation, in particular in subjects having a neurodegenerative, autoimmune, infectious, toxic or traumatic disorder. The invention also discloses new compositions and methods for treating neuroinflammatory diseases, such as multiple sclerosis.

BACKGROUND OF THE INVENTION

Neuroinflammation mainly involves the presence and activation, in neural tissue, of two types of immune cells: microglia (Stoll & Jander, 1999) and leukocytes (Man et al., 2007), causing local release of immune mediators. Microglial cells are resident cells of the central nervous system (CNS) (Kreutzberg, 1996), which participate in its immune surveillance and defence. They are activated under pathological conditions and acquire functions that finally lead to degeneration processes by damaging or killing neurons (Tilleux & Hermans, 2007). Leukocytes are located throughout the body, including the blood and lymphatic system. Under physiological condition, only small numbers of leukocytes such as T lymphocytes are present in CNS parenchyma. Their passage is limited by the blood-brain-barrier (BBB) (Wekerle et al., 1986; Hickey et al., 1991; Carvey et al., 2005), which is a hermetic barrier made of endothelial cells that controls the access of blood stream elements to the CNS (Rubin & Staddon, 1999; Prat et al., 2001). Under pathological condition, hematogenous leukocytes readily leave blood stream and reach the parenchyma to participate to a destructive inflammatory response (Man et al., 2007; Cardona et al., 2008), since it has been shown that BBB integrity is impaired during inflammation (Lossinsky & Shivers, 2004).

Neuroinflammation has been proposed to be implicated in the progressive nature of neurodegenerative diseases (Block & Hong, 2005). Involvement of neuroinflammation is for example well-known in neurological disorders, such as Multiple sclerosis (MS), Alzheimer's disease (AD), Parkinson's disease (PD), Amyotrophic lateral sclerosis (ALS), Acute disseminated encephalomyelitis (ADEM) and Neuromyelitis optica (NMO).

Precise pathogenesis of AD remains unclear. However, it has been hypothesized that AD is manifested by BBB impairment and neuroinflammation. Indeed, an increased number of Ig (Ishii & Haga, 1976; Mann et al., 1982; Licandro et al., 1983) has been found in the brain parenchyma, as well as CD4 or CD8 T cells (Itagaki et al., 1988; Rogers et al., 1988; McGeer et al., 1989; Singh, 1997; Neumann, 2001) in the hippocampus and temporal cortex of AD patients. Major histocompatibility complex (MHC) class I and II molecules, involved in antigen presentation and binding to T cells have also been identified in areas showing hallmark pathology (Itagaki et al., 1988; Rogers et al., 1988; McGeer et al., 1989; Mattiace et al., 1990; Perlmutter et al., 1992; Gonzalez-Scarano & Baltuch, 1999; Szpak et al., 2001; Kim & de Vellis, 2005; Walker & Lue, 2005).

PD is another neurodegenerative disorder of unknown aetiology. BBB impairment has been hypothesized as a causative mechanism in PD (Kortekaas et al., 2005). It has been suggested that under inflammatory state, VCAM-1 and ICAM-1 receptors are upregulated, due to microglial release of proinflammatory cytokines (Neumann & Wekerle, 1998). This upregulation results in recruitment of T cells and monocytes that harbor the several adequate counter receptors (CD11a/CD18 (LFA-1) and very late antigen-4) (Neumann & Wekerle, 1998).

Acute disseminated encephalomyelitis (ADEM) is an immune-mediated inflammatory disorder of the CNS. It is a monophasic disease that can arise spontaneously. However, 5 to 25% of patients experience relapse (Marchioni et al., 2005; Tenembaum et al., 2002) with recurrent or multiphasic forms. Most important symptoms include fever, headache, drowsiness, seizures and coma. The mortality rate can reach 5% (Menge et al., 2007). The exact aetiology of ADEM is at present unknown. It is characterized by a widespread of demyelination in the white matter of the brain and spinal cord. It can also involve the cortex and deep gray matter structures. From a histological point of view, ADEM is characterized by perivenular infiltrates of T cells and macrophages, associated with demyelination. Axonal damage has also been identified in the brains of some patients (DeLuca et al., 2004; Ghosh et al., 2004). It has been suggested that ADEM may result of the activation of myelin-reactive T cell clones involved in a non-specific inflammatory process (Tenembaum et al., 2007). ADEM is compared to multiple sclerosis, since it involves autoimmune demyelination (Rust, 2000; Poser, 2008). No standard therapy exists for ADEM since results are generally obtained from case reports and small series. Treatments usually comprise nonspecific immunosuppressant therapy, such as steroids, immunoglobulin, or plasma exchange, which are used in other autoimmune diseases including MS (Tenembaum et al., 2007).

Neuromyelitis optica (NMO) is an infrequent autoimmune, inflammatory and demyelinating disease of the CNS that affects myelin of the neurons placed at the optic nerves and spinal cord. The disease can be either monophasic or relapsing (Ghezzi et al., 2004). Extensive inflammation of the optic nerve (optic neuritis) and spinal cord (myelitis) usually leads to severe, permanent, relapse-related neurologic impairment (e.g., blindness, paraplegia) within 5 years (Wingerchuk & Weinshenker, 2003). Hallmarks of NMO are inflammatory lesions, cavitation, necrosis and axonal pathology. They have been observed in both grey and white matter of the spinal cord and optic nerves (Lucchinetti et al., 2002). At disease onset, the brain parenchyma is normal or may demonstrate few nonspecific subcortical white matter changes. It has been suggested that asymptomatic brain lesions are frequent in NMO at a later stage of the disease (Pittock et al., 2006). Until recently, NMO was considered to be a variant of multiple sclerosis. However, clinical, neuroimaging, laboratory and pathological characteristics differ. For example, NMO attacks are not mediated by T cells but rather by B cells in an autoimmune manner (Lucchinetti et al., 2002). There is at the moment no established optimal treatment for NMO since no randomized controlled trials have been performed. At present, parenteral corticosteroids are widely employed as first-line treatment of optic neuritis and myelitis attacks (Mandler et al., 1998), whereas therapeutic plasmapheresis that aims at removing autoantibodies, immune complexes and inflammatory mediators from the plasma, is applied in the case of corticosteroids failure (Keegan et al., 2002; Lehmann et al., 2006).

Multiple sclerosis is considered as an inflammatory demyelinating disease of the CNS (Skaper, 2007; Lassmann et al., 2007). For 85% of patients, disease course begins with a phase of recurrent and reversible neurological troubles termed Relapsing-Remitting MS (RRMS). This condition appears by the third-fourth decade of life. It can last for years and decades, with alternate phases of attacks with relapses, during which the patients recuperate neurological function (Trapp & Nave, 2008). Attacks last from a few days to weeks, and remissions a few months to years. After 8 to 20 years, patients enter the Secondary Progressive MS (SPMS) that is characterized by a continuous and irreversible neurological decline. A rarer disease form named Primary Progressive MS (PPMS) affects 15% of MS patients. There are no relapses occurring in PPMS disease form and disease is progressive from the onset. It occurs later than RRMS form (39 vs 29 years). Fifty percent of MS patients are unable to perform household and employment responsibilities 10 years after disease onset, and 50% are nonambulatory 25 years after disease onset (Trapp & Nave, 2008). Morphological alterations in CNS anatomy lead to paralysis, sensory disturbances, lack of coordination, and visual impairment among the most common features. These alterations (detected by magnetic resonance imaging (MRI), histopathologic evaluations and disease course vary significantly among patients (Agrawal & Yong, 2007).

Multiple sclerosis (MS) is the most frequent non traumatic neurological disease among young adults in North America and Europe, with 3.6 and 2.0 cases per 100 000 person-years incidence for women and men respectively (Alonso & Hernan, 2008). Multiple factors such as genetics, environment and infectious agents are part of MS development. It is considered as a non-herited disease. However, one can inherit a greater susceptibility to acquiring MS and it has been proposed that MS is a complex disease involving multiple genes with a low penetrance (Olsson & Hillert, 2008). Increased risk of developing MS has also been associated with the major histocompatibility complex (MHC) class II (Trapp & Nave, 2008), including the HLA-DRB1 gene which accounts for 16 to 60% of the genetic susceptibility (Haines et al., 1998). This supports the involvement of immune system in MS physiopathology. Additional susceptibility genes have been associated with MS, such as Interleukin-7 and -2 receptor alpha chain that display a low odds ratio of 1.3 (Olsson & Hillert, 2008). Inflammation, breakdown of BBB, demyelination, and axonal transection are pathological features of acute MS lesions. In RRMS phase, disability is caused by focal areas of inflammation where myelin, oligodendrocytes (responsible of myelin formation) and axons are destroyed (Ganter et al., 1999; Bjartmar et al., 2000; Lovas et al., 2000; Trapp et al., 1998). Attention is primarily focused on demyelinated lesions in the white matter at the chronic stage of the disease. However, evidence has accumulated that large areas of grey matter are also affected in MS patients (Stadelmann et al., 2008). It has been shown that T cells (mainly MHC-class I restricted CD8+ T cells) participate actively to inflammation, in addition to activated microglia (Lassmann et al., 2007). Moreover, impairment of BBB has been observed (Hochmeister et al., 2006; Kirk et al., 2003), allowing T cells to enter CNS. Relapse lasts a few month and the patients recuperate neurological function, due to resolution of inflammation and remyelination (Trapp et al., 1998; Ferguson et al., 1997). Transition toward SPMS and PPMS stages occurs when CNS can no longer compensate for additional neuronal loss (Trapp et al., 1999). In SPMS and PPMS stages, focal demyelinated white matter lesions remain, but new inflammatory active demyelinating lesions are infrequent. The pre-existing active lesions expand slowly, showing a little myelin breakdown activity especially in margins. These lesions show moderate inflammatory infiltrates, principally composed of T cells (CD8+ T cells) and active microglia (Prineas et al., 2001). In addition, diffuse atrophy of the grey and white matter as well as 'normal-appearing white matter' (NAWM) are observed (Miller et al., 2002).

Disease mechanisms pertinent to neuroinflammation have often been inferred from the Experimental Autoimmune Encephalomyelitis (EAE), an animal model of MS. This model is induced by sensitization of animals with brain tissue, myelin or protein antigens or by passive transfer of autoreactive T cells (Lassmann, 2008). Animals develop an inflammatory demyelinating disease that closely looks like MS (Lassmann, 2008). This model also supports the hypothesis according to which MS is an autoimmune disease. Indeed immunological data show autoreactive T cells and autoantibodies in circulation and in the cerebrospinal fluid. Since inflammation is a main hallmark of acute MS lesions, aggressive anti-inflammatory strategies have been assessed during RRMS, performing neuroprotective effects. Interferon $\beta$ (IFN$\beta$) and glatiramer acetate (GA) are commonly used to treat RRMS. IFN$\beta$ inflammatory effects concern decrease of antigen presentation, apoptosis, and entry of immune cells into the CNS (Neuhaus et al., 2005). GA mimics myelin basic protein (MBP), a major component of CNS myelin. It reduces antigen presentation and stimulates T cell secretion of cytokines associated with anti-inflammatory or lymphocytes T helper 2 actions (Neuhaus et al., 2001). Natalizumab, a humanized monoclonal antibody specific for $\alpha$4 integrins, has also been proposed for the treatment of RRMS (Polman et al., 2006; O'Connor et al., 2004). Another study suggests a role of recombinant erythropoietin as a protective agent in MS, but numerous problems are associated with this strategy since the use of erythropoietin and erythropoietin-analogues leads to simultaneous targeting of both the erythropoietic and tissue-protective properties of erythropoietin (Konstantinopoulos et al., 2007).

There exists a need for efficient therapies for treating neuroinflammation. There is also a strong need in the art for novel and effective therapies for the treatment of diseases having a neuroinflammatory component, such as multiple sclerosis, Alzheimer's disease, Parkinson's disease, Amyotrophic lateral sclerosis, Acute disseminated encephalomyelitis and Neuromyelitis optica.

SUMMARY OF THE INVENTION

The purpose of the present invention is to provide new therapeutic approaches for the treatment of neuroinflammatory condition, in particular specific for neurological diseases.

The invention specifically provides novel compositions and methods for treating neuroinflammation by modulation (e.g., reduction or reversion) of such condition in a subject. In particular, the invention relates to combined therapies for treating neuroinflammation by affecting extravasation cascade.

More specifically, the invention relates to a composition comprising a combination of at least two compounds selected from irbesartan, idraparinux, otamixaban, SR48692, cilostazol, mecamylamine, and clopidogrel, or salts, prodrugs, derivatives, or sustained release formulations thereof, for use in the treatment of neuroinflammation.

The present invention also relates to compositions comprising compounds that modify leukocyte extravasation cascade by modulating endothelium permeability, extracellular matrix formation, cell adhesion and motility, shear stress on endothelium and platelets aggregation. Preferred compositions for treating neuroinflammation, comprise a combination of at least two compounds selected from the group consisting of a modulator of endothelium permeability, a modulator of extracellular matrix formation, a modulator of cell adhesion and motility, modulator of shear stress on endothelium and a modulator of platelets aggregation, or salts or prodrugs or derivatives or sustained release formulations thereof.

The compositions according to the invention may be used for treating neuroinflammation in a subject having a neurodegenerative, autoimmune, infectious, toxic or traumatic disorder. Preferably, the compositions according to the invention are used for treating neuroinflammation in a subject having multiple sclerosis (MS).

In this regard, a particular object of the invention relates to a composition for use in the treatment of multiple sclerosis, comprising a combination of at least two compounds selected from the group consisting of irbesartan, idraparinux, otamixaban, SR48692, mecamylamine, cilostazol, clopidogrel, or salts or prodrugs or derivatives or sustained release formulations thereof.

Another particular object of the invention relates to a composition comprising a combination of at least mecamylamine and clopidogrel, or salts, prodrugs, derivatives or sustained release formulations thereof.

Another particular object of the invention relates to a composition comprising a combination of at least mecamylamine and clopidogrel, or salts, prodrugs, derivatives or sustained release formulations thereof, for use in the treatment of multiple sclerosis.

In an alternative embodiment, the composition according to the invention comprises a combination of at least two compounds chosen from the group consisting of irbesartan, idraparinux, otamixaban and SR48692, salts, prodrugs, derivatives or sustained release formulations thereof.

In a further alternative embodiment, the composition according to the invention comprises a combination of at least irbesartan, idraparinux, otamixaban and SR48692, salts, prodrugs, derivatives or sustained release formulations thereof.

A further object of the invention relates to a method for treating neuroinflammation in a human or animal subject, comprising administering to said subject, in need thereof, an effective amount of a composition of the invention.

A further object of the invention relates to a method for treating multiple sclerosis in a subject, comprising administering to said subject, in need thereof, an effective amount of a composition of the invention.

As will be further disclosed in the present application, the compounds of the compositions of the invention may be administered simultaneously, separately, sequentially and/or repeatedly in a same subject.

A further object of the invention relates to a method for assessing neuroinflammation treatment efficacy in a subject, wherein cells derived from the subject are exposed in vitro to a composition of the invention.

BRIEF LEGEND TO THE FIGURES

FIG. 1: Evolution of global clinical score upon mecamylamine and clopidogrel combinatory treatment. Global clinical score of EAE model mice is analyzed during the 28 days following the immunization. Treatment is constituted by clopidogrel hydrogen sulfate (270 µg/kg/day orally given, SIGMA, 098K46261) and mecamylamine hydrochloride (9 µg/kg/day orally given, TOCRIS, 1A/92335). Clinical score mean of each group (n=10 mice for each group) is figured +/− standard error mean for days 0, 5, 8, 9, 12, 14, 16, 19, 21, 23, 26 and 28 days after immunization (meca+clopi means mecamylamine and clopidogrel combinatory treatment).

DETAILED DESCRIPTION OF THE INVENTION

The present invention provides new therapeutic approaches for treating neuroinflammation and neuroinflammatory diseases. The invention discloses novel compositions and methods, which allow an effective correction of such diseases and may be used in any mammalian subject.

In particular, the inventors have identified several compounds which, in combination(s), can effectively affect biological pathways leading to neuroinflammation, by modulating specific stages of pathological migration of immune cells across the blood-brain-barrier.

Within the context of the invention, the term "neuroinflammation" designates a pathological condition characterized by a damage or destruction of neural tissue (such as without limitation cells of the central nervous system, including e.g., neuronal or glial cells (e.g. oligodendrocytes), or their specific fragments, such as neurites, axons, or myelin) resulting from induction of immune cells. In particular, neuroinflammation may be provoked by the activation of microglial cells releasing proinflammatory cytokines and/or by the activation of T and/or B cells and/or monocytes/marcophages. The term "neuroinflammation" particularly includes pathological conditions characterized or caused by extravasation of leukocytes across the blood-brain-barrier into the brain parenchyma, following such processes as e.g., rolling, activation, adhesion, locomotion, protrusion, and/or transmigration of leukocytes.

Within the context of the invention, the term "neuroinflammatory disorder or neuroinflammatory disease" designates a disease having a neuroinflammation component such as, in particular a neurodegenerative, autoimmune, infectious, toxic or traumatic disorder, where inflammatory component could be aetiological or pathology-exacerbating factor. Preferably, said neurodegenerative, autoimmune, infectious, toxic or traumatic diseases with inflammatory component include multiple sclerosis (MS), Alzheimer's disease (AD), Parkinson's disease (PD), Amyotrophic lateral sclerosis (ALS), Acute disseminated encephalomyelitis (ADEM) and Neuromyelitis optica (NMO).

Within the context of the invention, the term "treatment" includes the curative therapy, prevention, prophylaxis, retardation or reduction of pain and distress provoked by neuroinflammation or by neuroinflammatory diseases as defined above. The term treatment includes in particular the control of neuroinflammation progression and associated symptoms.

Within the context of the invention, the term "compound or drug" designates the chemical compounds as specifically named in the application or identified with its corresponding CAS number, as well as any pharmaceutically acceptable salt, hydrate, ester, ether, isomers, racemate, conjugates, prodrugs thereof of any purity.

Also, the term "combination or combinatorial therapy or combinatory treatment" designates a treatment wherein at least two or more compounds are co-administered to a subject to cause a biological effect. In a combined therapy according to this invention, the at least two drugs may be administered together or separately, at the same time or sequentially. Also, the at least two drugs may be administered through different routes and protocols. As a result, although they may be formulated together, the drugs of a combination may also be formulated separately.

The combinatorial therapies of the invention mainly target biological pathways, which have been identified by the inventors as involved in neuroinflammation. More specifically, a comprehensive analysis of results of cell biology experiments, pan-genomic expression profiling and genetic association studies revealing molecular and cellular mechanisms underlining pathophysiological characteristics of neuroinflammation, have allowed the inventors to decipher biological pathways involved in neuroinflammatory conditions, and to create a biological model of neuroinflammation networks of deregulated cellular pathways, leading to damage of neural tissue. The inventors prioritized functional networks linked to migration of immune cells in CNS through blood-brain-barrier, a key step in pathogenesis of neuroinflammation and neuronal disorders that comprise an important inflammatory part.

Interaction of immune cells with endothelium compartment is a complex stepwise process strictly controlled at cellular and molecular levels. Transendothelial migration of immune cells into damaged tissues (extravasation) is recognized as a key physiological process, which is implicated both in innate and adaptive immunity, and therefore, plays a protective role under normal conditions or could lead to uncontrolled tissue destruction, when deregulated by pathological stimuli.

Inflammatory stimuli, such as histamine or cytokines TNFα or IL-1, provoke profound functional remodelling of endothelial cells and transform them to effective mediators of recruitment and passage of leukocytes to damaged tissues. Activated endothelial cells are able to capture chemokines, produced by other cells on their surface and thereby, create optimal microenvironment for leukocyte adhesion on primed endothelium.

Adhesion of leukocytes to endothelium includes selectin-dependent transient capture and rolling of leukocytes on endothelium, followed by chemokine-triggered leukocyte arrest. Transition from slow rolling stage to leukocytes arrest on endothelium is mediated by leukocyte integrins, which bind to their ligands, for example ICAM1/2 and VCAM1, expressed on endothelial cells (Campbell et al., 1998).

The strong and specific adherence of leukocytes to endothelium, stimulated by inflammatory stimuli, is finalized by migration (diapedesis) of immune cells through the layer of endothelial cells and basement membrane into extravascular damaged tissues. Leukocyte migration occurs either through cellular contacts in endothelium (junctional pathway) or through cytoplasm of endothelial cells (transcellular pathway) (Jordan and Sessa, 2007; Vestweber, 2007).

At the last steps of leukocyte extravasation from vascular system, immune cells need to penetrate endothelial basement membrane and sheath of pericytes. Migration of leukocyte through basement membrane depends on activation of the β1-, β2- and β3-integrin families and cell-surface leukocyte proteases, which facilitate interaction of leukocyte receptors with extracellular ligands or generate chemotactic gradients inside extracellular matrix.

Therefore, migration of leukocytes through endothelium is assured by tight cooperation between immune and endothelial cells, and is accompanied by their functional remodelling, which is manifested by changes in endothelium permeability and by activation of cell adhesion and motility pathways in endothelial and immune cells. Additionally, adaptive changes in shear stress conditions and extracellular matrix formation seem to create optimal microenvironment for productive interaction between endothelial and immune cells and successful leukocyte migration into inflamed tissues. Consequently, passage of leukocytes through endothelium could be modulated by numerous external stimuli, provided by other cell types, for example, by muscle cells, pericytes, mast cells or activated platelets.

The inventors have identified and tested the combination of drugs that target the extravasation process, and modify it to improve the condition of patients suffering of neuroinflammation and neuroinflammatory diseases (such as neurodegenerative, autoimmune, infectious, toxic or traumatic disorders with inflammatory components). The different functional elements of this extravasation process have been analyzed, as discussed above, and numerous molecules have been targeted as important positive or negative modulators of leukocyte transmigration.

More specifically, the inventors have selected a number of compounds, which, in combination, alter one or more of the biological functions affected in neuroinflammatory conditions. More specifically, these compounds are able to modulate principal functional pathways implicated, as has been described above, in leukocyte extravasation, namely: remodelling of endothelium permeability, cell adhesion and motility, extracellular matrix formation, shear stress conditions and platelets aggregation, as promising candidates for combinatorial therapeutic intervention in context of human neuroinflammatory diseases.

Compounds of the invention that modify leukocyte extravasation cascade include:

modulators of remodeling of endothelium permeability, preferably selected from bosentan (CAS number 147536-97-8), fondaparinux (CAS number 114870-03-0), pentazocine (CAS number 359-83-1), nifuroxazide (CAS number 965-52-6), tiludronate (CAS number 89987-06-4), gliclazide (CAS number 21187-98-4), irbesartan (CAS number 138402-11-6), loperamide (CAS number 53179-11-6), modulators of cell adhesion and motility preferably selected from terbinafine (CAS number 91161-71-6), lithium carbonate (CAS number 554-13-2), valproic acid (CAS number 99-66-1), diosmin (CAS number 520-27-4), captopril (CAS number 62571-86-2), metformin (CAS number 657-24-9), ketoprofen (CAS number 22071-15-4), cromoglicate (CAS number 16110-51-3), bacitracin (CAS number 1405-87-4), eflornithine (CAS number 67037-37-0), benzbromarone (CAS number 3562-84-3), SR48692 (IUPAC Name: 2-[[1-(7-chloroquinolin-4-yl)-5-(2,6-dimethoxyphenyl) pyrazole-3-carbonyl]amino]adamantane-2-carboxylic acid), glibenclamide (CAS number 10238-21-8), tranexamic acid (CAS number 1197-18-8), modulators of extracellular matrix formation preferably selected from argatroban (CAS number 74863-84-6), lisinopril (CAS number 83915-83-7), quinapril (CAS number 85441-61-8), ramipril (CAS number 87333-19-5), idraparinux (CAS number 162610-17-5), otamixaban (CAS number 193153-04-7), enoxaparin (CAS number 9005-49-6), disulfiram (CAS number 97-77-8), spironolactone (CAS number 52-01-7), modulators of shear stress on endothelium preferably selected from amlodipine (CAS number 88150-42-9), clonidine (CAS number 4205-90-7), liothyronine (CAS number 6893-02-3), diltiazem (CAS number 42399-41-7), gentamicin (CAS number 1403-66-3), neomycin (CAS number 1404-04-2), mecamylamine (CAS number 60-40-2), streptomycin (CAS number 57-92-1), and modulators of platelets aggregation, preferably inhibitors of platelets aggregation, preferably selected from cilostazol (CAS number 73963-72-1), tirofiban (CAS number 144494-65-5), clopidogrel (CAS number 113665-84-2), ticlopidine (CAS number 55142-85-3).

The present invention provides new therapeutic approaches for treating neuroinflammation, in particular in a subject having a neurodegenerative, autoimmune, infectious or toxic disease. The invention discloses novel use of compound combinations which allow an effective correction of such diseases and may be used in any mammalian subject.

These compound combinations are particularly advantageous because they affect different pathways and thus are more effective. These compounds include potent modifiers of functional modules associated with extravasation cascade processes, which can, in complementary, additive or synergic manner, reduce or minimize neuroinflammation in central nervous system.

Taking into account functional complexity of extravasation cascade targeted by the present invention, the inventors consider combinatorial treatment as the most appropriate approach for effective therapeutic modulation and treating of neuroinflammation conditions.

Further, the inventors have identified combinations of drugs, which target functional modules implicated in consecutive phases of extravasation cascade and therefore, characterized by increased therapeutic efficacy in comparison with therapeutic efficacies of individual drugs. The inventors demonstrate that this approach can be used for development of combinatorial therapies, which contain preferably ultra-low doses of active compounds, and thereby, potentially allows to decrease undesirable secondary effects of individual drugs.

Typical compositions of the invention comprise a combination of 2 compounds, 3 compounds or 4 compounds selected from the group consisting of a modulator of endothelium permeability, a modulator of extracellular matrix formation, a modulator of cell adhesion and motility, an inhibitor of platelets aggregation and a modulator of shear stress on endothelium, or salts or prodrugs or derivatives or sustained release formulations thereof. More complex combinations may also be considered. These compounds may be formulated together or separately, and administered together, separately or sequentially.

In specific embodiments, the composition of the invention comprises at least one of the following combinations of compounds, for combined, separate or sequential administration:
- at least one modulator of endothelium permeability (preferably selected from bosentan, fondaparinux, pentazocine, nifuroxazide, tiludronate, gliclazide, irbesartan, loperamide) and at least one inhibitor of platelets aggregation (preferably selected from cilostazol, tirofiban, clopidogrel, ticlopidine);
- at least one modulator of extracellular matrix formation (preferably selected from argatroban, lisinopril, quinapril, ramipril, idraparinux, otamixaban, enoxaparin, disulfiram, spironolactone) and least one inhibitor of platelets aggregation (preferably selected from cilostazol, tirofiban, clopidogrel, ticlopidine);
- at least one modulator of cell adhesion and motility (preferably selected from terbinafine, lithium carbonate, valproic acid, diosmin, captopril, metformin, cromoglicate, bacitracin, eflornithine, benzbromarone, SR48692, glibenclamide, tranexamic acid) and at least one inhibitor of platelets aggregation (preferably selected from cilostazol, tirofiban, clopidogrel, ticlopidine);
- at least one modulator of shear stress on endothelium (preferably selected from amlodipine, clonidine, liothyronine, diltiazem, gentamicin, mecamylamine, neomycin, streptomycin) and at least one inhibitor of platelets aggregation (preferably selected from cilostazol, tirofiban clopidogrel, ticlopidine);
- at least one modulator of extracellular matrix formation (preferably selected from argatroban, lisinopril, quinapril, ramipril, idraparinux, otamixaban, enoxaparin, disulfiram, spironolactone) and at least one modulator of endothelium permeability (preferably selected from bosentan, fondaparinux, pentazocine, nifuroxazide, tiludronate, gliclazide, irbesartan, loperamide);
- at least one modulator of extracellular matrix formation (preferably selected from argatroban, lisinopril, quinapril, ramipril, idraparinux, otamixaban, enoxaparin, disulfiram, spironolactone) and at least one modulator of cell adhesion and motility (preferably selected from terbinafine, lithium carbonate, valproic acid, diosmin, captopril, metformin, cromoglicate, bacitracin, eflornithine, benzbromarone, SR48692, glibenclamide, tranexamic acid);
- at least one modulator of cell adhesion and motility (preferably selected from terbinafine, lithium carbonate, valproic acid, diosmin, captopril, metformin, cromoglicate, bacitracin, eflornithine, benzbromarone, SR48692, glibenclamide, tranexamic acid) and at least one modulator of endothelium permeability (preferably selected from bosentan, fondaparinux, pentazocine, nifuroxazide, tiludronate, gliclazide, irbesartan, loperamide);
- at least one modulator of cell adhesion and motility (preferably selected from terbinafine, lithium carbonate, valproic acid, diosmin, captopril, metformin, cromoglicate, bacitracin, eflornithine, benzbromarone, SR48692, glibenclamide, tranexamic acid) and at least one modulator of shear stress on endothelium (preferably selected from amlodipine, clonidine, liothyronine, diltiazem, gentamicin, mecamylamine, neomycin, streptomycin);
- at least one modulator of endothelium permeability (preferably selected from bosentan, fondaparinux, pentazocine, nifuroxazide, tiludronate, gliclazide, irbesartan, loperamide) and at least one modulator of shear stress on endothelium (preferably selected from amlodipine, clonidine, liothyronine, diltiazem, gentamicin, mecamylamine, neomycin, streptomycin).

A particular object of the invention relates to a composition comprising at least one modulator of extracellular matrix formation, preferably idraparinux or otamixaban, and at least one inhibitor of platelets aggregation, preferably cilostazol, clopidogrel, ticlopidine or tirofiban.

Another particular object of the invention relates to a composition comprising at least one modulator of cell adhesion and motility, preferably terbinafine, bacitracin, tranexamic acid, diosmin or SR48692 and at least one inhibitor of platelets aggregation, preferably cilostazol, clopidogrel, ticlopidine or tirofiban.

A further object of the invention relates to a composition comprising at least one modulator of extracellular matrix formation, preferably idraparinux, otamixaban, or argatroban, and at least one modulator of cell adhesion and motility, preferably tranexamic acid or neurotensin receptor antagonist SR48692.

A further object of the invention relates to a composition comprising at least one modulator of endothelium permeability, preferably irbesartan, and at least one inhibitor of platelets aggregation, preferably cilostazol, clopidogrel, ticlopidine or tirofiban.

A further object of the invention relates to a composition comprising at least one modulator of shear stress on endothelium, preferably mecamylamine, and at least one inhibitor of platelets aggregation, preferably clopidogrel, cilostazol, ticlopidine or tirofiban.

A further object of the invention relates to a composition for treating neuroinflammation, comprising at least:
- a modulator of endothelium permeability, preferably irbesartan,
- a modulator of extracellular matrix formation, preferably idraparinux or otamixaban,
- a modulator of cell adhesion and motility, preferably SR48692,
- a modulator of shear stress on endothelium, preferably mecamylamine, and
- an inhibitor of platelets aggregation, preferably clopidogrel or cilostazol.

According to another embodiment, a composition of the invention comprises at least a modulator of endothelium permeability (preferably selected from bosentan, fondaparinux, pentazocine, nifuroxazide, tiludronate, gliclazide, irbesartan, loperamide), a modulator of extracellular matrix formation (preferably selected from argatroban, lisinopril, quinapril, ramipril, idraparinux, otamixaban, enoxaparin, disulfiram, spironolactone), a modulator of cell adhesion and motility (preferably selected from terbinafine, lithium carbonate, valproic acid, diosmin, captopril, metformin, cromoglicate, bacitracin, eflornithine, benzbromarone, SR48692, glibenclamide, tranexamic acid), a modulator of shear stress on endothelium (preferably selected from amlodipine, clonidine, liothyronine, diltiazem, gentamicin, mecamylamine, neomycin, streptomycin) and an inhibitor of platelets aggregation (preferably selected from cilostazol, tirofiban, clopidogrel, ticlopidine).

More preferred combination therapies for neuroinflammation comprise a combination of at least two compounds selected from irbesartan, idraparinux, otamixaban, SR48692, cilostazol, mecamylamine and clopidogrel, or salts or prodrugs thereof.

The most preferred compositions for treating neuroinflammation, comprise at least one of the following combinations of compounds:
- Idraparinux and Irbesartan,
- Idraparinux and Mecamylamine,
- Irbesartan and SR4896,
- Irbesartran and Mecamylamine,
- Mecamylamine and Clopidogrel,
- Otamixaban and SR4896,
- Otamixaban and Clopidogrel,
- SR4896 and Mecamylamine,
- SR4896 and Clopidogrel,
- Cilostazol and Idraparinux,
- Cilostazol and Irbesartan,
- Cilostazol and Mecamylamine,
- Cilostazol and SR4896,
- Idraparinux and Otamixaban,
- Idraparinux and SR4896,
- Idraparinux and Clopidogrel,
- Irbesartan and Otamixaban,
- Otamixaban and Mecamylamine,
- Cilostazol and Otamixaban,
- Mecamylamine and Clopidogrel and Otamixaban,
- Mecamylamine and Cilostazol and Idraparinux,
- Mecamylamine and Clopidogrel and Irbesartan,
- Mecamylamine and Clopidogrel and Idraparinux,
- Mecamylamine and Clopidogrel and SR48692,
- Mecamylamine and Cilostazol and Irbesartan,
- Mecamylamine and Cilostazol and Otamixaban, or
- Mecamylamine and Cilostazol and SR48692.

All combination therapies according to the invention may also be used for treating neuroinflammatory diseases such as neurodegenerative, autoimmune, infectious, toxic or traumatic diseases with a neuroinflammatory component, for example multiple sclerosis (MS).

In a particular embodiment, all the compositions according to the invention can be used for treating neuroinflammation in subjects having neurodegenerative disorders.

The invention further provides a method for treating neuroinflammation, comprising administering to a subject in need thereof an effective amount of any combination of compounds of compositions as disclosed above. A preferred method comprises the administration of a combination of at least two compounds described above or salts or prodrugs or derivatives or sustained release formulations thereof.

Any of the various uses or methods of treatment disclosed herein can also include an optional step of diagnosing a patient as having neuroinflammation, or identifying an individual as at risk of developing neuroinflammation.

A further object of this invention is a method for treating neuroinflammation in a subject, comprising administering simultaneously, separately or sequentially to said subject, in need of such a treatment, an effective amount of any combination of at least two compounds of compositions mentioned above, or salts or prodrugs thereof.

In this regard, a further object of this invention is a method of treating neuroinflammation, the method comprising (1) assessing whether a subject has neuroinflammatory disease and (2) treating the subject having this disease with an effective amount of a composition according to the invention. Determining whether a subject has neuroinflammation can be done by various tests known per se in the art.

Another particular object of the invention resides in a method for assessing neuroinflammation treatment efficacy in a subject, wherein cells derived from the subject are exposed in vitro to a composition of the invention.

The invention may be used for treating neuroinflammation or neuroinflammatory disease in any mammalian subject, particularly human subjects.

As illustrated in Table 1, the combination therapies of the invention induce a positive response in treating of neuroinflammation.

The compounds of compositions according to the present invention can be administered simultaneously, separately or sequentially in a same subject. In other embodiments, said compounds are formulated in solid or liquid dosage forms, for single or repeated administration to a patient. Preferably, the compositions of the invention further comprise one or more pharmaceutically acceptable excipients.

Therapy according to the invention may be performed as drug combination and/or in conjunction with any other therapy. It may be provided at home, the doctor's office, a clinic, a hospital's outpatient department, or a hospital, so that the doctor can observe the therapy's effects closely and make any adjustments that are needed.

The duration of the therapy depends on the stage of the disease being treated, the age and condition of the patient, and how the patient responds to the treatment.

The dosage, frequency and mode of administration of each component of the combination can be controlled independently. For example, one drug may be administered orally while the second drug may be administered intramuscularly. Combination therapy may be given in on-and-off cycles that include rest periods so that the patient's body has a chance to recovery from any as yet unforeseen side-effects. The drugs may also be formulated together such that one administration delivers both drugs.

Formulation of Pharmaceutical Compositions

The administration of each drug of the combination may be by any suitable means that results in a concentration of the drug that, combined with the other component, is able to diminish neuroinflammation.

While it is possible for the active ingredients of the combination to be administered as the pure chemical, it is preferable to present them as a pharmaceutical composition, also referred to in this context as pharmaceutical formulation. Possible compositions of the invention include those suitable for oral, rectal, intrathecal, percutaneous, mucosal, topical (including transdermal, buccal and sublingual), or parenteral (including subcutaneous, intramuscular, intravenous and intradermal) administration. The compositions of the invention may also be administered by inhalation.

More commonly these pharmaceutical formulations are prescribed to the patient in "patient packs" containing a number dosing units or other means for administration of metered unit doses for use during a distinct treatment period in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions. Thus, the invention further includes a pharmaceutical formulation, as herein before described, in combination with packaging material suitable for said formulations. In such a patient pack the intended use of a formulation for the combination treatment can be inferred by instructions, facilities, provisions, adaptations and/or other means to help using the formulation most suitably for the treatment. Such measures make a patient pack specifically suitable for and adapted for use for treatment with the combination of the present invention.

The drug may be contained in any appropriate amount in any suitable carrier substance, and may be present in an amount of 1-99% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active drug substantially immediately upon administration or at any predetermined time or time period after administration.

The controlled release formulations include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance; (iv) formulations that localize drug action by, e.g., spatial placement of a controlled release regimen adjacent to or in the diseased tissue or organ; and (v) formulations that target drug action by using carriers or chemical derivatives to deliver the drug to a particular target cell type.

Administration of drugs in the form of a controlled release formulation is especially preferred in cases in which the drug, either alone or in combination, has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD50) to median effective dose (ED50)); (ii) a narrow absorption window in the gastro-intestinal tract; or (iii) a very short biological half-life so that frequent dosing during a day is required in order to sustain the plasma level at a therapeutic level.

Any of a number of strategies can be pursued in order to obtain controlled release in which the rate of release outweighs the rate of metabolism of the drug in question. Controlled release may be obtained by appropriate selection of various formulation parameters and ingredients, including, e.g., various types of controlled release compositions and coatings. Thus, the drug is formulated with appropriate excipients into a pharmaceutical regimen that, upon administration, releases the drug in a controlled manner (single or multiple unit tablet or capsule compositions, oil solutions, suspensions, emulsions, microcapsules, microspheres, nanoparticles, patches, and liposomes).

Solid Dosage Forms for Oral Use

Formulations for oral use include tablets containing the active ingredient(s) in a mixture with non-toxic pharmaceutically acceptable excipients. These excipients may be, for example, inert diluents or fillers (e.g., sucrose, microcrystalline cellulose, starches including potato starch, calcium carbonate, sodium chloride, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., acacia, alginic acid, sodium alginate, gelatin, starch, pregelatinized starch, microcrystalline cellulose, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., stearic acid, silicas, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). A time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology.

The two compounds may be mixed together in the tablet, or may be partitioned. For example, the first compound is contained on the inside of the tablet, and the second compound is on the outside, such that a substantial portion of the second compound is released prior to the release of the first compound.

Formulations for oral use may also be presented as chewable tablets, or as hard gelatin capsules wherein the active ingredient is mixed with an inert solid diluent (e.g., potato starch, microcrystalline cellulose, calcium carbonate, calcium phosphate or kaolin), or as soft gelatin capsules wherein the active ingredient is mixed with water or an oil medium, for example, liquid paraffin, or olive oil. Powders and granulates may be prepared using the ingredients mentioned above under tablets and capsules in a conventional manner.

Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of drugs, or by incorporating the drug into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the compounds of the claimed combinations may also be in the form of a buoyant tablet or capsule (i.e., a tablet or capsule that, upon oral administration, floats on top of the gastric content for a certain period of time). A buoyant tablet formulation of the drug(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable suspending agents are, for example, sodium carboxymethylcellulose, methylcellulose, sodium alginate, and the like.

Parenteral Compositions

The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation or it may be presented as a dry powder to be reconstituted with water or another suitable vehicle before use. Apart from the active drug(s), the composition may include one or more suitable parenterally acceptable carriers and/or excipients. The active drug(s) may be incorporated into microspheres, microcapsules, nanoparticles, liposomes, or the like for controlled release. The composition may include suspending, solubilizing, stabilizing, pH-adjusting agents, and/or dispersing agents.

The pharmaceutical compositions according to the invention may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the drugs is only sparingly or slightly soluble in water, a dissolution enhancing or solubilizing agent can be added, or the solvent may include 10-60% w/w of propylene glycol or the like.

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(glycolic acid) or poly(ortho esters).

Rectal Compositions

For rectal application, suitable dosage forms for a composition include suppositories (emulsion or suspension type), and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols. Various additives, enhancers, or surfactants may be incorporated.

Percutaneous and Topical Compositions

The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

The Emulsifying Agents May be Naturally Occurring Gums (e.g., Gum Acacia or Gum Tragacanth)

The preservatives, humectants, penetration enhancers may be parabens, such as methyl or propyl p-hydroxybenzoate, and benzalkonium chloride, glycerin, propylene glycol, urea, etc.

The pharmaceutical compositions described above for topical administration on the skin may also be used in connection with topical administration onto or close to the part of the body that is to be treated. The compositions may be adapted for direct application or for application by means of special drug delivery devices such as dressings or alternatively plasters, pads, sponges, strips, or other forms of suitable flexible material.

Dosages and Duration of the Treatment

It will be appreciated that the drugs of the combination may be administered concomitantly, either in the same or different pharmaceutical formulation or sequentially. If there is sequential administration, the delay in administering the second (or additional) active ingredient should not be such as to lose the benefit of the efficacious effect of the combination of the active ingredients. A minimum requirement for a combination according to this description is that the combination should be intended for combined use with the benefit of the efficacious effect of the combination of the active ingredients. The intended use of a combination can be inferred by facilities, provisions, adaptations and/or other means to help using the combination according to the invention.

Therapeutically effective amounts of two or more drugs that are subjects of this invention can be used together for the preparation of a medicament useful for reducing neuroinflammation once it has become clinically manifest or to prevent this condition for patients at risk.

Although the active drugs of the present invention may be administered in divided doses, for example two or three times daily, a single daily dose of each drug in the combination is preferred, with a single daily dose of all drugs in a single pharmaceutical composition (unit dosage form) being most preferred.

Administration can be one to several times daily for several days to several years, and may even be for the life of the patient. Chronic or at least periodically repeated long-term administration will be indicated in most cases.

The term "unit dosage form" refers to physically discrete units (such as capsules, tablets, or loaded syringe cylinders) suitable as unitary dosages for human subjects, each unit containing a predetermined quantity of active material or materials calculated to produce the desired therapeutic effect, in association with the required pharmaceutical carrier.

The amount of each drug in the combination preferred for a unit dosage will depend upon several factors including the administration method, the body weight and the age of the patient, the severity of neuroinflammation process or risk of potential side effects considering the general health status of the person to be treated.

Additionally, pharmacogenomic (the effect of genotype on the pharmacokinetic, pharmacodynamic or efficacy profile of a therapeutic) information about a particular patient may affect the dosage used.

Except when responding to especially impairing neuroinflammation when higher dosages may be required, or when treating children when lower dosages should be chosen, the preferred dosage of each drug in the combination will usually lie within the range of doses not above the usually prescribed for long-term maintenance treatment or proven to be safe in the large phase 3 clinical studies.

Preferably, ultra-low doses of active compounds are used in drug combinations according to the invention, thereby allowing to decrease undesirable secondary effects of each drug. More specifically, these ultra-low doses are sub-therapeutic doses, i.e., doses which are lower than therapeutic doses usually prescribed, preferably ½ of therapeutic doses, more preferably ⅓, ¼, ⅕, or even more preferably ⅒ of therapeutic doses. In particular examples, doses as low as 1/20, 1/30, 1/50, 1/100, or even lower, of therapeutic doses are used. At such sub-therapeutic dosages, the compounds alone would be substantially inactive, while the combination(s) according to the invention are fully effective.

Examples of preferred dosages for drugs in drug combinations according to the invention are:

Irbesartan orally less than 15 mg per day,
Cilostazol orally less than 10 mg per day,
Clopidogrel orally less than 7.5 mg per day,
Mecamylamine orally less than 0.25 mg per day.

It will be understood that the amount of the drug actually administered will be determined by a physician, in the light of the relevant circumstances including the condition or conditions to be treated, the exact regimen to be administered, the age, weight, and response of the individual patient, the severity of the patient's symptoms, and the chosen route of administration. Therefore, the above dosage ranges are intended to provide general guidance and support for the teachings herein, but are not intended to limit the scope of the invention.

The following examples are given for purposes of illustration and not by way of limitation.

EXAMPLES

Example 1

Protocol for the Induction of EAE in C57BL/6 Mice

A model in which myelin-oligodendrocyte glycoprotein-immunized (MOG-immunized) mice develop chronic progressive EAE is used to demonstrate the beneficial effect of compositions of the invention in neuroinflammation treatment.

I— Animals and Chemicals

SJL and C57BL/6J mice are purchased from Janvier (France). C57BL/6 mice, female of 6- to 9-week-old (Optimal: 7-week-old); Complete Freund's adjuvant (CFA): mixing 20 mL IFA (Adjuvant Incomplete Freund, DIFCO 263910) with 100 mg *M. tuberculosis* H37 Ra (killed and desiccated, DIFCO 231141); 3 mM MOG35-55 peptide (MEVGWYRSPFSRVVHLYRNGK, SEQ ID NO:1) stock dissolved in PBS.

II—Procedure

The experimental encephalomyelitis is induced by following procedure:

Day 0:

Prepare the emulsion containing MOG35-55 stock, PBS and CFA. The volume of MOG35-55 stock=[(The volume of the emulsion)×(1.5 g/L)]/[(3×10-3 mol/L)×(2581.6 g/mol)]; the volume of PBS=[(The volume of the emulsion)/2]−(The volume of MOG35-55 stock); The volume of CFA=(The volume of the emulsion)/2. The emulsion is prepared by diluting the MOG35-55 stock with PBS and then mix equal volumes of this diluent and CFA. The final concentration of MOG35-55 is 300 µg per 200 µL emulsion for each mouse. Air bubbles should be avoided and the syringe must be kept at 4° C. until injection. Before use the stability of the emulsion is tested by adding one drop into a beaker of water: if the drop remains as a solid clump and slowly dissipates, then the emulsion is stable and may be injected.

Mice are anesthetized with 2% Pentobarbital sodium (i.p injection, 70~90 µL/mouse) and kept warm under infrared lamp. Injection of 200 ng Pertussis toxin in 200 µL PBS/mouse is performed (i.v.; tail vein) using a 1-mL syringe with 0.4-mm needle. The previously described emulsion is subcutaneously administered with a 1-mL syringe with 0.4-mm needle.

Day 2:

Mice are kept warm under infrared lamp to perform injection of 200 ng Pertussis toxin in 200 µL PBS via i.v. (tail vein) route, as described for MOG35-55 injection.

Days 0~70:

Mice are daily observed for clinical symptoms.

III—Clinical Score 0.0: No sign of disease 0.5: Partial paralysis of the tail: flaccidity and absence of curling in the distal half of the tail when mouse is picked up.

1.0: When mouse is picked up, one can observe a complete paralysis of the tail associated to flaccidity and absence of curling at the tip.

1.5: Weakness of one hind paw that does not allow mouse to hang on by one hind foot (the other hind foot is normal). When hanging on by the joint of the hind limb, this is not counted in the score.

2.0: Weakness of both hind paws: mouse cannot hang on by any of its hind feet. Mouse waddles along and has difficulty to raise its rump up completely with the hind paws.

2.5: Hind paw paralysis:

Partial paralysis of both hind paws resulting in the difficulty to move the paws.

Complete paralysis in one hind paw resulting in the impossibility to move it. By walking, this paw trails behind the mouse.

To allow mouse to feed, water and food are given on the cage floor.

3.0: Complete hind paw paralysis although fore-paws are not affected by pathology. Mouse can still hang on thanks to its fore paws. To allow mouse to feed, water and food are given on the cage floor.

3.5: Partial fore-paw paralysis including a complete paralysis of one fore-paw or partial paralysis of both.

4.0: Complete fore-paws paralysis. Moribund state.

5.0: Death of animal or sacrifice for experimental ethics.

Animals are kept in a conventional pathogen-free facility and all experiments are carried out in accordance with guidelines prescribed by, and are approved by, the standing local committee of bioethics.

Statistics

Statistica software (Statsoft Inc.) is utilized throughout for statistical analysis. ANOVA analysis and Student's t test are employed to analyze clinical disease score. $P<0.05$ is considered significant.

Acute Drug Treatment

Inhibition of Acute Onset EAE and Chronic EAE is assessed by tissue analysis (detection of the presence of perivascular lymphocyte infiltrate) as well as by clinical scoring and body mass weighting.

The acute onset study is performed for 28 days after EAE induction.

Females are divided into groups of 12 mice before EAE induction. The treatment is administered during 3 weeks before EAE induction and further throughout the whole experiment.

Clopidogrel and mecamylamine are administered alone or in combinations orally (clopidogrel) and subcutaneously (mecamylamine). Mecamylamine, at one of the doses (0.04 mg/kg; 0.2 mg/kg; 1 mg/kg/day), and a placebo control is delivered via subcutaneous osmotic minipump over 6 weeks. After 6 weeks, animals are anesthetized, and a small incision is made in the skin after preparation for aseptic surgery. The pump is then replaced with a new pump and drug or placebo is delivered over a next period of time.

Clopidogrel (dosed from 0.02 mg/kg/day to 1 mg/kg/day) is administered as clopidogrel tablets dissolved in drinking water, Plavix, Bristol-Myers Squibb/Sanofi). The upper dose is known to be effective and safe based on results from experiments testing drug toxicity in rats (Reist M. et al. 2000).

All animals are daily examined for behavioural tests. The observations are performed by experimentator who does not know identity of treatments.

At the end of experiment, mice are intracardiacally perfused with saline. Spinal cord and brain tissues are removed and postfixed in formalin and then embedded in paraffin. Sections of 2-4 micrometer are collected and stained with Hematoxylin and Eosin to be examined under light microscope for the presence of perivascular lymphocyte infiltrate inflammation. Scores are then attributed as no inflammation, mild, moderate and severe as described (Mohamed, 2004).

The Interpretation of Results

1 Histological examination at day 28 reveals that majority of animals in the group treated with the combination of clopidogrel and mecamylamine have no inflammation (no signs of perivascular cuffing), with the rest of the animals showing only mild perivascular cuffing in the spinal section, while the animals from the placebo group and from the groups treated with clopidogrel or mecamylamine alone are characterized by different degrees of perivascular inflammation.

This difference between the group treated with the combination of two drugs and the control placebo groups reaches statistical significance (p value less than 0.05).

2 In comparison to the mice receiving vehicle, the mice receiving the combination of clopidogrel and mecamylamine exhibit a significantly lower mean clinical score (p value less than 0.05) at day 28 of the experiment than mice from all other experimental groups of animals induced for EAE. These results demonstrate that this combination decreases the severity of EAE, as compared to control placebo group.

Chronic Drug Treatment.

A chronic phase study is run for 70 days post EAE induction.

All treated animals are receiving the treatment during three weeks prior to EAE induction. The combined clopidogrel and mecamylamine are administered alone or in combinations orally (clopidogrel) and subcutaneously (mecamylamine). Mecamylamine, at one of three doses (0.05 mg/kg; 0.2 mg/kg, 1 mg/kg/day), and a placebo control is delivered via subcutaneous osmotic minipump over 6 weeks. After 6 weeks, animals are anesthetized, and a small incision is made in the skin after preparation for aseptic surgery. The pump is then replaced with a new pump and drug or placebo is delivered over a next period of time.

Clopidogrel (20 mg/kg/day) is administered as clopidogrel tablets dissolved in drinking water, Plavix, Bristol-Myers Squibb/Sanofi).

For the study female animals are divided into groups of 12 mice each and subjected to EAE induction.

All animals are examined for behavioural deficits daily; the examinations are done by an experimenter who is blinded as to the treatments they received. All control animals treated with placebo are symptomatic at 11-24 days.

The Interpretation of Results

In comparison to the mice receiving vehicle, the mice receiving the combination of clopidogrel and mecamylamine exhibit a significantly lower mean clinical score (p value less than 0.05) at day 70 of the experiment than mice from all other experimental groups of animals induced for EAE. These results demonstrate that this combination decreases the severity of EAE, as compared to control placebo group.

The differences in weight gain are correlated with the disease severity, i.e., stronger disease severity (higher mean clinical score) provokes a greater weight loss. These differences are statistically significant ($p<0.005$, Manova). The subsequent Post Hoc comparison demonstrates that all the groups treated with clopidogrel or mecamylamine are different from the control group treated with placebo (vehicle) whereas the initial mean weights of all the groups are equal. On day 14, three days after the onset of the disease, a sick mice loses an average of 2 g of weight. The average mean weight of mice treated with the combination of clopidogrel and mecamylamine is reduced by only 0.4 g. On day 28 the control group has the lowest weight, 14.0 g.

The group treated with the combination of clopidogrel and mecamylamine is comparable with the positive control on day 28 (statistically there is no difference between these two groups) and significantly different from the sick mice treated with the placebo on day 70.

Example 2

In a particular experimental setting adapted for correct comparison of therapeutic effects of clopidogrel, mecamylamine and their combination in mouse EAE model, only acute drug treatment regimen is used (the treatment starts at Day 14 after the immunization and lasts until the Day 28). In this experiment, both drugs are equally diluted to ultra-low doses corresponding to 1/60 of their usual therapeutic doses, and importantly, both are administered orally. Protocols for EAE induction and clinical score calculations in this experiment are slightly modified and are described in detail below:

I. Animals and Chemicals

C57L/6J female mice (8 weeks old) are purchased from Janvier (France); after two weeks of habituation, female mice (10 weeks old) develop chronic paralysis after immunization with MOG (Myelin Oligodendrocyte Glycoprotein) peptide. The experimental encephalomyelitis is induced with the Hooke Kit $MOG_{35-55}$/CFA Emulsion PTX (Pertussis toxin) for EAE Induction (EK-0110, EK-0115; Hooke laboratories). The control kit is CK-0115 (Hooke laboratories).

II. Experimental Procedure

The experimental encephalomyelitis is induced by following procedure:

The day 0, two subcutaneous injections of 0.1 ml each are performed; one on upper back of the mouse and one in lower back. Each injection contains 100 μg of $MOG_{35-55}$ peptide (MEVGWYRSPFSRVVHLYRNGK), 200 μg of inactivated *Mycobacterium tuberculosis* H37Ra and is emulsified in Complete Freund's adjuvant (CFA) (Hooke laboratories). The emulsion provides antigen needed to expand and differentiate MOG-specific autoimmune T cells.

Two intraperitoneal injections of 500 ng of Pertussis toxin in PBS (Hooke kit) are performed 2 hours (Day 0) and 24 hours (Day 1) after the MOG injection. Pertussis toxin enhances EAE development by providing additional adjuvant.

Mice develop EAE 8-14 days after immunization and stay chronically paralyzed for the duration of the experiment. After the immunization, mice are daily observed for clinical symptoms in a blind procedure. Animals are kept in a conventional pathogen-free facility and all experiments are carried out in accordance with guidelines prescribed by, and are approved by, the standing local committee of bioethics.

Statistics.

Statistica software (Statsoft Inc.) is utilized throughout for statistical analysis. ANOVA analysis and Student's t test are employed to analyze clinical disease score. $P<0.05$ is considered significant.

III. Clinical Scores:

The total clinical score is composed of the tail score, the hind limb score, the fore limb score and the bladder score described as below:

Tail Score:

| | |
|---|---|
| Score = 0 | A normal mouse holds its tail erect when moving. |
| Score = 1 | If the extremity of the tail is flaccid with a tendency to fall. |
| Score = 2 | If the tail is completely flaccid and drags on the table. |

Hind Limbs Score:

| | |
|---|---|
| Score = 0 | A normal mouse has an energetic walk and doesn't drag his paws |
| Score = 1 | Either one of the following tests is positive: A—Flip test: while holding the tail between thumb and index finger, flip the animal on his back and observe the time it takes to right itself. A healthy mouse will turn itself immediately. A delay suggests hind-limb weakness. B—Place the mouse on the wire cage top and observe as it crosses from one side to the other. If one or both limbs frequently slip between the bars we consider that there is a partial paralysis. |
| Score = 2 | Both previous tests are positive. |
| Score = 3 | One or both hind limbs show signs of paralysis but some movements are preserved; for example: the animal can grasp and hold on to the underside of the wire cage top for a short moment before letting go. |
| Score = 4 | When both hind legs are paralyzed and the mouse drags them when moving. |

Fore Limbs Score:

| | |
|---|---|
| Score = 0 | A normal mouse uses its front paws actively for grasping and walking and holds its head erect. |
| Score = 1 | Walking is possible but difficult due to a weakness in one or both of the paws, for example, the front paws are considered weak when the mouse has difficulty grasping the underside of the wire top cage. Another sign of weakness is head drooping. |

| | |
|---|---|
| Score = 2 | When one forelimb is paralyzed (impossibility to grasp and the mouse turns around the paralyzed limb). At this time the head has also lost much of its muscle tone. |
| Score = 3 | Mouse cannot move, and food and water are unattainable. |

Bladder Score:

| | |
|---|---|
| Score = 0 | A normal mouse has full control of its bladder. |
| Score = 1 | A mouse is considered incontinent when its lower body is soaked with urine. |

The global score for each animal is determined by the addition of all the above mentioned categories. The maximum score for live animals is 10.

Experimental Groups and Drug Treatment:

Three different groups of 10 female mice are homogenized by weight before the immunization:

Control group: vehicle injection in the same conditions of EAE mice (from Day 14 to Day 28, placebo is given daily)

EAE group: MOG injection (day 0)+Pertussis toxin injections (Day 0 and 1)–from Day 14 to Day 28, placebo is given orally daily EAE+treatment group: MOG injection (Day 0)+Pertussis toxin injections (Day 0 and 1). The treatment starts at Day 14 after the immunization and lasts until the Day 28.

The clinical scores are measured at Days 0-5-8-9-12-14-16-19-21-23-26-28.

Interpretation of the Results

As expected, the first paralysis signs appeared 14 days after the immunization (Day 0): on the FIG. 1, we observe an increase of the global clinical score (mean of tail, fore limb, hind limb and bladder scores) of the EAE group (grey triangles line) compared to the control mice (grey diamonds line) from this day until the end of the experiment (Day 28). From Day 16 to Day 28 after immunization, a tendency of the clopidogrel and mecamylamine combinatory treatment (black circles line) to decrease the clinical score of the EAE mice in comparison with EAE mice without treatment is observed. Strikingly, no positive effects of clopidogrel or mecamylamine, which are tested alone at the same concentrations as in the combinatory treatment, are obtained in this experimental setting.

These experiments demonstrate that therapeutic combination of clopidogrel and mecamylamine, modifying two different functional processes implicated in extravasation cascade-platelet aggregation and shear stress on endothelium, is more effective in suppressing MS phenotype than individual drugs, administered separately. In this particular experimental setting, clopidogrel and mecamylamine are used at doses corresponding to 1/60 of the doses, routinely prescribed for these medications. Clopidogrel was never tested as a potential therapeutic for treating multiple sclerosis; in non-related inflammatory conditions, for example, like chronic renal injury or diabetic retinal ischemia, where this drug had some beneficial effect, it was administered at doses 30-60 times higher than in our experiments (De La Cruz et al., 2003; Tu et al., 2008).

Positive results are also obtained with other drug combinations listed in Table 1.

TABLE 1

Other drug combinations which give positive results

| Drug combinations | Results* |
|---|---|
| Idraparinux-Irbesartan | + |
| Idraparinux-Otamixaban | + |
| Idraparinux-SR4896 | + |
| Idraparinux-Mecamylamine | + |
| Idraparinux-Clopidogrel | + |
| Irbesartan-Otamixaban | + |
| Irbesartan-SR4896 | + |
| Irbesartan-Mecamylamine | + |
| Otamixaban-SR4896 | + |
| Otamixaban-Mecamylamine | + |
| Otamixaban-Clopidogrel | + |
| SR4896-Mecamylamine | + |
| SR4896-Clopidogrel | + |
| Cilostazol-Idraparinux | + |
| Cilostazol-Irbesartan | + |
| Cilostazol-Otamixaban | + |
| Cilostazol-Mecamylamine | + |
| Cilostazol-SR4896 | + |
| Mecamylamine-Clopidogrel-Irbesartan | + |
| Mecamylamine-Clopidogrel-Idraparinux | + |
| Mecamylamine-Clopidogrel-Otamixaban | + |
| Mecamylamine-Clopidogrel-SR48692 | + |
| Mecamylamine-Cilostazol-Irbesartan | + |
| Mecamylamine-Cilostazol-Idraparinux | + |
| Mecamylamine-Cilostazol-Otamixaban | + |
| Mecamylamine-Cilostazol-SR48692 | + |

*+ (positive results) designates a decrease of the global clinical score (composed of the tail score, the hind limb score, the fore limb score and the bladder score as defined above) in comparison with subjects without treatment.

REFERENCES

Adair-Kirk T L et al. A site on laminin α5, AQARSAASKVKVSMKF, induces inflammatory cell production of matrix metalloproteinase-9 and chemotaxis. J. Immunol. 2003; 171: 398-406.

Agrawal S M & Yong V W. Immunopathogenesis of multiple sclerosis. Int Rev Neurobiol. 2007; 79: 99-126.

Alonso A & Hernan M A. Temporal trends in the incidence of multiple sclerosis: a systematic review. Neurology. 2008; 71: 129-35.

Bjartmar C et al. Neurological disability correlates with spinal cord axonal loss and reduced N-acetyl aspartate in chronic multiple sclerosis patients. Ann Neurol. 2000; 48: 893-901.

Block M L & Hong J S. Microglia and inflammation-mediated neurodegeneration: multiple triggers with a common mechanism. Prog Neurobiol. 2005; 76: 77-98.

Campbell, J. J et al. Chemokines and the arrest of lymphocytes rolling under flow conditions. Science 1998; 279: 381-384.

Cardona A E et al. Chemokines in and out of the central nervous system: much more than chemotaxis and inflammation. J Leukoc Biol. 2008; 84: 587-94.

Carvey P M et al. 6-Hydroxydopamine-induced alterations in blood-brain barrier permeability. Eur J Neurosci. 2005; 22: 1158-68.

Cree B A et al. Neuromyelitis optica. Semin Neurol. 2002; 22: 105-22.

De La Cruz et al. Effects of clopidogrel and ticlopidine on experimental diabetic ischemic retinopathy in rats. Naunyn Schmiedebergs Arch Pharmacol. 2003; 367: 204-210.

DeLuca G C et al. Axonal loss in multiple sclerosis: a pathological survey of the corticospinal and sensory tracts. Brain. 2004; 127: 1009-18.

Ferguson B et al. Axonal damage in acute multiple sclerosis lesions. Brain. 1997; 120 (Pt 3): 393-9.

Ganter P et al. Spinal cord axonal loss in multiple sclerosis: a post-mortem study. Neuropathol Appl Neurobiol. 1999; 25: 459-67.

Ghezzi A et al. Clinical characteristics, course and prognosis of relapsing Devic's Neuromyelitis Optica. J Neurol. 2004; 251: 47-52.

Ghosh N et al. Evidence of axonal damage in human acute demyelinating diseases. J Neurol Sci. 2004; 222: 29-34.

Gonzalez-Scarano F & Baltuch G. Microglia as mediators of inflammatory and degenerative diseases. Annu Rev Neurosci. 1999; 22: 219-40.

Haines J L et al. Linkage of the MHC to familial multiple sclerosis suggests genetic heterogeneity. The Multiple Sclerosis Genetics Group. Hum Mol Genet. 1998; 7: 1229-34.

Hochmeister S et al. Dysferlin is a new marker for leaky brain blood vessels in multiple sclerosis. J Neuropathol Exp Neurol. 2006; 65: 855-65.

Ishii T & Haga S. Immuno-electron microscopic localization of immunoglobulins in amyloid fibrils of senile plaques. Acta Neuropathol. 1976; 36: 243-9.

Itagaki S et al. Presence of T-cytotoxic suppressor and leucocyte common antigen positive cells in Alzheimer's disease brain tissue. Neurosci Lett. 1988; 91: 259-64.

Jordan, S P & Sessa, P W C Evolving functions of endothelial cells in inflammation. Nature Reviews Immunology 2007; 7:803-815.

Keegan M et al. Plasma exchange for severe attacks of CNS demyelination: predictors of response. Neurology. 2002; 58: 143-6.

Kim S U & de Vellis. Microglia in health and disease. J Neurosci Res. 2005; 81: 302-13.

Kirk J et al. Tight junctional abnormality in multiple sclerosis white matter affects all calibres of vessel and is associated with blood-brain barrier leakage and active demyelination. J Pathol. 2003; 201: 319-27.

Konstantinopoulos P A et al. Selective modulation of the erythropoietic and tissue-protective effects of erythropoietin: time to reach the full therapeutic potential of erythropoietin. Biochim Biophys Acta. 2007; 1776: 1-9.

Kortekaas R et al. Blood-brain barrier dysfunction in parkinsonian midbrain in vivo. Ann Neurol. 2005; 57: 176-9.

Kreutzberg G W Microglia: a sensor for pathological events in the CNS. Trends Neurosci. 1996; 19: 312-8.

Lassmann H et al. The immunopathology of multiple sclerosis: an overview. Brain Pathol. 2007; 17: 210-8.

Lassmann H. Models of multiple sclerosis: new insights into pathophysiology and repair. Curr Opin Neurol. 2008; 21: 242-7.

Lehmann H C et al. Plasma exchange in neuroimmunological disorders: Part 1: Rationale and treatment of inflammatory central nervous system disorders. Arch Neurol. 2006; 63: 930-5.

Licandro A et al. Alzheimer's disease and senile brains: an immunofluorescence study. Riv Patol Nery Ment. 1983; 104: 75-87.

Lossinsky A S & Shivers R R. Structural pathways for macromolecular and cellular transport across the blood-brain barrier during inflammatory conditions. Review. Histol Histopathol. 2004; 19: 535-64.

Lovas G et al. Axonal changes in chronic demyelinated cervical spinal cord plaques. Brain. 2000; 123 (Pt 2): 308-17.

Lucchinetti C F et al. A role for humoral mechanisms in the pathogenesis of Devic's neuromyelitis optica. Brain. 2002; 125: 1450-61.

Man S et al. Inflammatory cell migration into the central nervous system: a few new twists on an old tale. Brain Pathol. 2007; 17: 243-50.

Mandler R N et al. Devic's neuromyelitis optica: a prospective study of seven patients treated with prednisone and azathioprine. Neurology. 1998; 51: 1219-20.

Mann D M et al. Immunohistochemical staining of senile plaques. Neuropathol Appl Neurobiol. 1982; 8: 55-61.

Marchioni E et al. Postinfectious inflammatory disorders: subgroups based on prospective follow-up. Neurology. 2005; 65: 1057-65.

Mattiace L A et al. Detection of HLA-DR on microglia in the human brain is a function of both clinical and technical factors. Am J Pathol. 1990; 136: 1101-14.

McGeer P L et al. Immune system response in Alzheimer's disease. Can J Neurol Sci. 1989; 16: 516-27.

Menge T et al. Acute disseminated encephalomyelitis: an acute hit against the brain. Curr Opin Neurol. 2007; 20: 247-54.

Miller D H et al. Measurement of atrophy in multiple sclerosis: pathological basis, methodological aspects and clinical relevance. Brain. 2002; 125: 1676-95.

Mohamed A et al. The use of digital technology to assess the severity of the Experimental Allergic Encephalomyelitis (EAE) spinal cord lesion. Biomed Sci Instrum. 2004; 40:419-23.

Neuhaus O et al. Mechanisms of action of glatiramer acetate in multiple sclerosis. Neurology. 2001; 56: 702-8.

Neuhaus O et al. Putative mechanisms of action of statins in multiple sclerosis—comparison to interferon-beta and glatiramer acetate. J Neurol Sci. 2005; 233: 173-7.

Neumann H. Control of glial immune function by neurons. Glia. 2001; 36: 191-9.

Neumann H & Wekerle H. Neuronal control of the immune response in the central nervous system: linking brain immunity to neurodegeneration. J Neuropathol Exp Neurol. 1998; 57: 1-9.

O'Connor P W et al. Randomized multicenter trial of natalizumab in acute MS relapses: clinical and MRI effects. Neurology. 2004; 62: 2038-43.

Olsson T & Hillert J. The genetics of multiple sclerosis and its experimental models. Curr Opin Neurol. 2008; 21: 255-60.

Perlmutter L S et al. MHC class II-positive microglia in human brain: association with Alzheimer lesions. J Neurosci Res. 1992; 33: 549-58.

Pittock S J et al. Brain abnormalities in neuromyelitis optica. Arch Neurol. 2006; 63: 390-6.

Polman C H et al. A randomized, placebo-controlled trial of natalizumab for relapsing multiple sclerosis. N Engl J Med. 2006; 354: 899-910.

Poser C M. Multiple sclerosis and recurrent disseminated encephalomyelitis are different diseases. Arch Neurol. 2008; 65: 674; author reply 674-5.

Prat A et al. Glial cell influence on the human blood-brain barrier. Glia. 2001; 36: 145-55.

Prineas J W et al. Immunopathology of secondary-progressive multiple sclerosis. Ann Neurol. 2001; 50: 646-57.

Reist M, et al. Very slow chiral inversion of clopidogrel in rats: a pharmacokinetic and mechanistic investigation. Drug Metab Dispos. 2000; 28: 1405-1410.

Rogers J et al. Expression of immune system-associated antigens by cells of the human central nervous system: relationship to the pathology of Alzheimer's disease. Neurobiol Aging. 1988; 9: 339-49.

Rubin L L & Staddon J M. The cell biology of the blood-brain barrier. Annu Rev Neurosci. 1999; 22: 11-28.

The invention claimed is:

1. A method for treating a neuroinflammation in a mammalian subject, comprising administering simultaneously or separately an effective amount of a combination of (i) an inhibitor of platelet aggregation selected from the group consisting of clopidogrel, cilostazol, ticlopidine, tirofiban, and salts thereof, and (ii) a compound selected from the group consisting of mecamylamine (CAS number 60-40-2), irbesartan, idraparinux, otamixaban, SR48692, salts thereof, and sustained release formulations thereof to said mammalian subject having said neuroinflammation, wherein a clinical score of said neuroinflammation is decreased.

2. The method of claim 1, wherein said combination comprises at least one of the following combinations of compounds:

Mecamylamine (CAS number 60-40-2) and Clopidogrel,
Otamixaban and Clopidogrel,
SR48692 and Clopidogrel,
Idraparinux and Clopidogrel,
Cilostazol and Idraparinux,
Cilostazol and Irbesartan,
Cilostazol and Mecamylamine (CAS number 60-40-2),
Cilostazol and SR48692,
Mecamylamine (CAS number 60-40-2) and Clopidogrel and Otamixaban,
Mecamylamine (CAS number 60-40-2) and Clopidogrel and Irbesartan,
Mecamylamine (CAS number 60-40-2) and Clopidogrel and Idraparinux,
Mecamylamine (CAS number 60-40-2) and Clopidogrel and SR48692,
Mecamylamine (CAS number 60-40-2) and Cilostazol and Irbesartan,
Mecamylamine (CAS number 60-40-2) and Cilostazol and Otamixaban, or
Mecamylamine (CAS number 60-40-2) and Cilostazol and SR48692.

3. The method of claim 1, wherein said neuroinflammation is caused by multiple sclerosis (MS).

4. The method of claim 1, wherein said compounds are formulated in solid or liquid dosage forms, with one or several pharmaceutically acceptable excipients, for single or repeated administration to the subject.

5. The method of claim 1, wherein said combination of compounds is administered by oral, parenteral, intrathecal, topical, percutaneous or mucosal route or by inhalation.

SEQUENCE LISTING

<160> NUMBER OF SEQ ID NOS: 1

<210> SEQ ID NO 1
<211> LENGTH: 21
<212> TYPE: PRT
<213> ORGANISM: Mouse

<400> SEQUENCE: 1

Met Glu Val Gly Trp Tyr Arg Ser Pro Phe Ser Arg Val Val His Leu
1               5                   10                  15

Tyr Arg Asn Gly Lys
            20

6. The method of claim 1, wherein the inhibitor of platelet aggregation is clopidogrel, a salt thereof, or sustained release formulation thereof.

7. The method of claim 1, which comprises administering to the subject an effective amount of a combination of Mecamylamine (CAS number 60-40-2) and Clopidogrel, salts thereof or sustained release formulations thereof.

8. A method for treating multiple sclerosis in a mammalian subject, comprising administering simultaneously or separately to said subject in need thereof, an effective amount of a combination of (i) an inhibitor of platelet aggregation selected from the group consisting of clopidogrel, cilostazol, ticlopidine, tirofiban, and salts thereof, and (ii) a compound selected from the group consisting of mecamylamine (CAS number 60-40-2), irbesartan, idraparinux, otamixaban, SR48692, salts thereof, and sustained release formulations thereof, wherein a clinical score of multiple sclerosis is decreased.

9. The method of claim 8, which comprises administering to the subject a combination of mecamylamine (CAS number 60-40-2) and clopidogrel, salts thereof, or sustained release formulations thereof.

\* \* \* \* \*

UNITED STATES PATENT AND TRADEMARK OFFICE
CERTIFICATE OF CORRECTION

Page 1 of 1

PATENT NO. : 8,642,566 B2
APPLICATION NO. : 13/260773
DATED : February 4, 2014
INVENTOR(S) : Daniel Cohen, Serguei Nabirochkin and Ilya Chumakov It is certified that error appears in the above-identified patent and that said Letters Patent is hereby corrected as shown below:

In the Specification

Column 2,
Line 29, "may result of" should read --may result from--.

Column 13,
Lines 17-18, "a number dosing units" should read --a number of dosing units--.

Column 16,
Line 17, "in form of" should read --in the form of--.

Column 17,
Line 5, "pharmaceutical" should read --pharmaceutically--.

Column 21,
Lines 36-37, "a sick mice" should read --a sick mouse--.

Column 25,
Line 57, "Nery Ment." should read --Nerv Ment.--.

Column 27,
Line 23, "523-36." should read --S23-36.--.

Signed and Sealed this
Twentieth Day of January, 2015

Michelle K. Lee
*Deputy Director of the United States Patent and Trademark Office*